United States Patent
Sohn et al.

(10) Patent No.: US 10,555,923 B2
(45) Date of Patent: Feb. 11, 2020

(54) METHOD FOR TREATING PAROXYSMAL NOCTURNAL HEMOGLOBINURIA

(71) Applicant: ENZYCHEM LIFESCIENCES CORPORATION, Chungcheongbuk-do (KR)

(72) Inventors: Ki Young Sohn, Seoul (KR); Jae Wha Kim, Daejeon (KR)

(73) Assignee: Enzychem Lifesciences Corporation, Chungcheongbuk-do (KR)

( * ) Notice: Subject to any disclaimer, the term of this patent is extended or adjusted under 35 U.S.C. 154(b) by 0 days.

(21) Appl. No.: 15/775,810

(22) PCT Filed: Nov. 14, 2016

(86) PCT No.: PCT/KR2016/013077
§ 371 (c)(1),
(2) Date: May 11, 2018

(87) PCT Pub. No.: WO2017/082708
PCT Pub. Date: May 18, 2017

(65) Prior Publication Data
US 2018/0296520 A1    Oct. 18, 2018

Related U.S. Application Data

(60) Provisional application No. 62/255,416, filed on Nov. 14, 2015.

(51) Int. Cl.
| | |
|---|---|
| A61K 31/231 | (2006.01) |
| A61K 9/48 | (2006.01) |
| A61P 7/00 | (2006.01) |
| A61K 31/355 | (2006.01) |

(52) U.S. Cl.
CPC .......... A61K 31/231 (2013.01); A61K 9/4825 (2013.01); A61K 31/355 (2013.01); A61P 7/00 (2018.01); *A61K 2300/00* (2013.01)

(58) Field of Classification Search
CPC ............ A61K 31/231; A61K 9/48; A61P 7/00
USPC ....................................................... 514/547
See application file for complete search history.

(56) References Cited

U.S. PATENT DOCUMENTS

| | | | |
|---|---|---|---|
| 2014/0243548 A1 | 8/2014 | Lee et al. | 554/151 |
| 2015/0266803 A1 | 9/2015 | Lee et al. | 554/151 |
| 2016/0256428 A1 | 9/2016 | Kim et al. | 514/547 |

FOREIGN PATENT DOCUMENTS

| | | |
|---|---|---|
| KR | 10-2006-0047447 | 5/2006 |
| KR | 10-2015-0021464 | 3/2015 |
| WO | WO 1999/026640 | 6/1999 |
| WO | WO 2005/112912 | 12/2005 |
| WO | WO 2013/043009 | 3/2013 |
| WO | WO 2015/176012 | 11/2015 |

OTHER PUBLICATIONS

Schafer et al. Drug Discovery Today, 2008, 13 (21/22), 913-916.*
Horig et al. Journal of Translational Medicine 2004, 2(44), p. 1-8.*
Yang et al. Biol Pharm Bull, (2004), 27(7), p. 1121-1125 (provided by Applicants and disclosed in IDS).*
Hwang et al, Immune Network, (Jun. 2015), 15(3), p. 150-156 (provided by Applicants and disclosed in IDS).*
Letter/Written Disclosure of the Information Disclosure Statement for the above-referenced application, filed herewith on May 22, 2018, 2 pages.
Hwang et al., "Effect of 1-palmitoyl-2-linoleoyl-3-acetyl-rac-glycerol on Immune Functions in Healthy Adults in a Randomized Controlled Trial," Immune Network 15(3):150-160 (2015).
Marti-Carvajal et al., "Eculizumab for treating patients with paroxysmal nocturnal hemoglobinuria," Cochrane Database of Systematic Reviews Issue 2, Art. No. CD010340, DOI: 10.1002/14651858. CD010340, 33 pages (2013).
Yang et al., "Stimulatory Effects of Monoacetyldiglycerides on Hematopoiesis," Biol. Pharm. Bull. 27(7):1121-1125 (2004).
Yang et al., "Purification and Structural Determination of Hematopoietic Stem Cell-Stimulating Monoacetyldiglycerides from *Cervus nippon* (Deer Antler)," Chem. Pharm. Bull. 52(7):874-878 (2004).
International Search Report, dated Feb. 14, 2017, in connection with International Patent Application No. PCT/KR2016/013077, 3 pages.
Written Opinion, dated Feb. 14, 2017, in connection with International Patent Application No. PCT/KR2016/013077 [English translation and original document in Korean], 15 pages.

* cited by examiner

*Primary Examiner* — Yong L Chu
(74) *Attorney, Agent, or Firm* — Mintz Levin Cohn Ferris Glovsky and Popeo, P.C.; Peter F. Corless

(57) ABSTRACT

The present invention provides methods for treating, controlling or mitigating paroxysmal nocturnal hemoglobinuria (PNH), comprising administering a monoacetyldiacylglycerol compound to a patient in need thereof, as well as compositions useful therefor.

19 Claims, 6 Drawing Sheets

METHOD FOR TREATING PAROXYSMAL NOCTURNAL HEMOGLOBINURIA

RELATED APPLICATIONS

This application is the U.S. National Stage application of PCT/KR2016/013077, filed Nov. 14, 2016, which claims benefit of priority from U.S. Provisional Application No. 62/255,416, filed Nov. 14, 2015, the specification of which is incorporated by reference herein.

TECHNICAL FIELD

The present invention relates to methods for treating, controlling or mitigating paroxysmal nocturnal hemoglobinuria (PNH), comprising administration of a monoacetyldiacylglycerol compound, as well as compositions useful therefor.

BACKGROUND

Paroxysmal nocturnal hemoglobinuria (PNH), also known as Marchiafava-Micheli syndrome, is a rare, acquired, life-threatening disease of the blood characterized by destruction of erythrocytes by the complement system.

Normally, blood cells are protected from complement destruction by proteins including decay-accelerating factor (DAF/CD55), which disrupts formation of C3-convertase, and protectin (CD59/MIRL/MAC-IP), which blocks formation of the membrane attack complex by preventing C9 from incorporating into the complex. These proteins, CD55 and CD59, are anchored to the cell membrane by glycosyl phosphatidylinositol (GPI), a glycolipid that is attached to the C-terminus of certain proteins during posttranslational modification. GPI comprises a phosphoethanolamine linker that attaches to the C-terminal of the protein, a glycan core, and a phospholipid moiety with hydrophobic lipid tails that anchor the protein-GPI structure to the cell membrane.

PNH patients have defects in GPI synthesis, so that the proteins, particularly CD55 and CD59, that protect the cell from destruction by complement are not properly anchored to the cell membrane. In the most common case, there is a somatic mutation in the gene for phosphatidylinositol N-acetylglucosaminyltransferase subunit A (PIGA), which is required for synthesis of N-acetylglucosaminyl phosphatidylinositol (GlcNAc-PI), which is the first intermediate in the biosynthetic pathway of GPI anchor. The PIGA gene is located on the X chromosome, which means that only one active copy of the gene for PIGA is present in each cell (males have only one X chromosome; in females the second X chromosome is silenced through X-inactivation). Mutation of the PIGA gene thus can lead to the absence of functional GPI anchors. When this mutation occurs in a hematopoietic stem cell (HSC), all of the subsequent progeny of this cell will have the same mutation. PNH may arise on its own ("primary PNH") or in the context of other bone marrow disorders such as aplastic anemia ("secondary PNH"). Because the mutation does not necessarily affect all progeny lines of erythrocytes, patients may have varying degrees of the disease, with only some, or most, or substantially all of the erythrocytes failing to present CD55 and CD59.

PNH can be diagnosed by measuring levels of CD55 and CD59 presentation on erythrocytes or by measuring GPI. In one method, flow cytometry for CD55 and CD59 on white and red blood cells is used to categorize erythrocytes as type I, II, or III PNH cells, wherein type I cells have normal levels of CD55 and CD59; type II have reduced levels; and type III have absent levels. In another method, fluorescein-labeled proaerolysin (FLAER), which binds selectively to the GPI, is used to measure GPI levels on erythrocytes.

Symptoms of PNH include red or dark urine due to the presence of hemoglobin and hemosiderin from the breakdown of red blood cells, as well as symptoms of anemia, such as tiredness, shortness of breath, and palpitations. Patients may have abdominal pain, difficulty swallowing and pain during swallowing, esophageal spasm, erectile dysfunction, headache, hypertension, and/or pulmonary hypertension. It is believed that these symptoms are caused by hemoglobin released during hemolysis, which binds circulating nitric oxide, thereby inhibiting relaxation of vascular smooth muscle. Blood clots may develop in common sites (deep vein thrombosis of the leg and resultant pulmonary embolism when these clots break off and enter the lungs), as well as the hepatic vein (causing Budd-Chiari syndrome), the portal vein of the liver (causing portal vein thrombosis), the superior or inferior mesenteric vein (causing mesenteric ischemia), veins of the skin, and in the brain (stroke).

Allogeneic bone marrow transplantation, to replace the defective HSCs with healthy HCSs, has significant risks, such as graft-vs-host disease or failure of the graft, and suitable donors may not be available. The monoclonal antibody eculizumab, which blocks terminal complement activation, reduces the need for blood transfusions and improves quality of life in PNH patients, but does not reduce overall mortality or the incidence of clots. See, Marti-Carvajal, A J, et al. "Eculizumab for treating patients with paroxysmal nocturnal hemoglobinuria," The Cochrane database of systematic reviews 10: CD010340 (30 Oct. 2014). Currently, treatment of PNH is most often symptomatic, with blood transfusions and supplementation with folic acid or iron for the anemia, and anticoagulants for the clotting. Transfusions, in addition to reducing the severity of the anemia, may suppress production of the defective PNH erythrocytes, thereby reducing damage to the small blood vessels by accumulation of damaged cells and reducing symptoms caused by hemoglobin released during hemolysis. PDE5 inhibitors may be used to mitigate the effect of hemoglobin binding to nitric oxide. Corticosteroids such as prednisolone, or other immunosuppressive drugs are sometimes used in an effort to suppress the complement-mediated destruction of the erythrocytes.

New approaches to the treatment and management of PNH are needed.

Deer antler is a traditional Asian medicine, prepared by drying uncornified antler of deer. Deer antler has been acclaimed to have various medical effects, such as growth- and development-promoting effects, promoting hematopoietic function, treating nervous breakdown, benefiting cardiac insufficiency, and improving the function of five viscera and six entrails, as described in the Dong-eui Bogam, a Korean medical book first published in 1613. It has been reported that certain components of deer antler, including rac-1-palmitoyl-2-linoleoyl-3-acetylglycerol (PLAG) obtained from chloroform extracts of the deer antler, have growth-stimulating activities of hematopoietic stem cells and megakaryocytes (WO 99/26640). It is also reported that monoacetyldiacylglycerol derivatives which are active components of the deer antlers are effective in treating autoimmune diseases, sepsis, cancers such as bile duct cancer, kidney cancer or malignant melanoma, and so on (WO 2005/112912). Use of certain monoacetyldiacylglycerol derivatives for treatment of leukopenia and/or thrombocytopenia is described, e.g., in International Application No. PCT/US2015/031204, the contents of which are incorporated herein by reference.

DETAILED DESCRIPTION OF THE INVENTION

Technical Problem

The disclosure of the present invention shows that the monoacetyldiacylglycerol of Formula 1 described herein, particularly, PLAG of Formula 2, reduces complement activity, is useful for protection against complement-mediated depletion of erythrocytes as seen in PNH, and is effective for treating PNH:

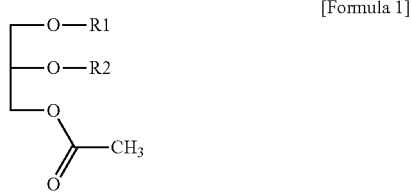

[Formula 1]

wherein $R_1$ and $R_2$ are independently a fatty acid residue of 14 to 22 carbon atoms.

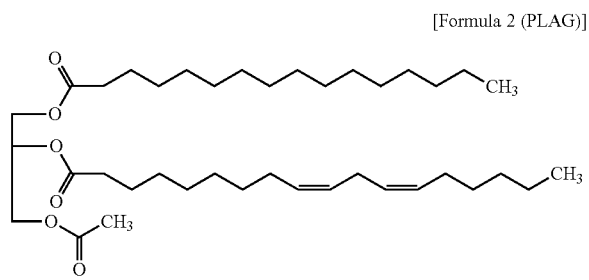 [SMILES: CCCCC/C=C\C/C=C\CCCCCCCC(=O)OC(CCOC(C)=O)COC(=O)CCCCCCCCCCCCCCC]

[Formula 2 (PLAG)]

Means for Solving the Technical Problem

In some embodiments, the present invention provides methods for treating, (e.g. inhibiting, reducing, controlling, mitigating, or reversing) paroxysmal nocturnal hemoglobinuria (PNH), comprising administering to a patient in need thereof an effective amount of a compound of Formula 2 (PLAG).

In addition, the present invention provides a pharmaceutical composition, including a functional health food, comprising a compound of Formula 1, for treating or improving PNH.

The present invention further provides the compound of Formula 1, and pharmaceutical compositions comprising the compound of Formula 1, for use in methods as described, and for use in the manufacture of medicaments for use in methods as described.

In one embodiment, the disclosure provides a novel pharmaceutical unit dose drug product, in the form of a soft gelatin capsule for oral administration containing 250-1,000 mg, e.g., 500 mg, of PLAG drug substance, substantially free of other triglycerides, together with 0.1-3 mg, e.g. 1 mg, of a pharmaceutically acceptable tocopherol compound, e.g., α-tocopherol, as an antioxidant, e.g., for administration once or twice a day, at a daily dosage of 500 mg to 4,000 mg.

Further areas of applicability of the present invention will become apparent from the detailed description and examples provided hereinafter. It should be understood that the detailed description and specific examples, while indicating certain preferred embodiments of the invention, are intended for purposes of illustration only and are not intended to limit the scope of the invention.

BEST MODE FOR CARRYING OUT THE INVENTION

Figure 1:
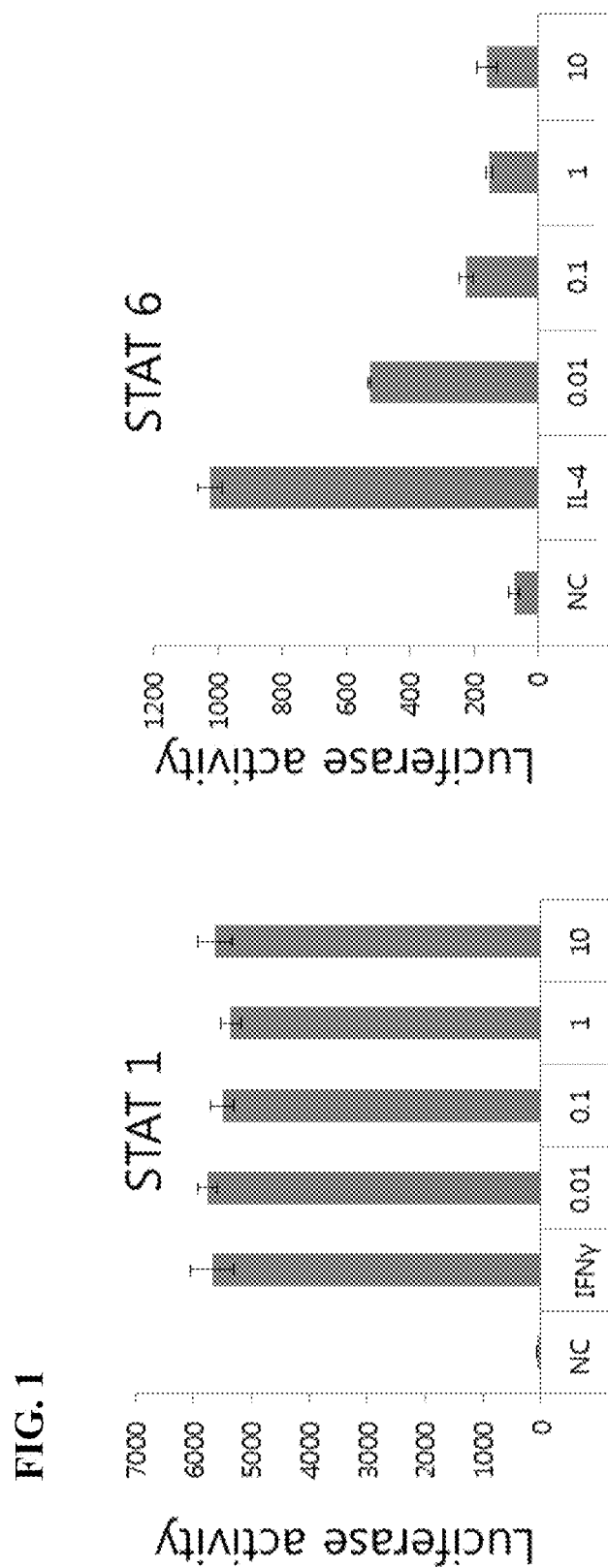
FIG. 1 depicts a reporter assay for STAT1 and STATE transcriptional activity in PLAG-treated HepG2 cells.

Compositions of the present invention for treating paroxysmal nocturnal hemoglobinuria (PNH) include glycerol derivatives having one acetyl group and two acyl groups of Formula 1:

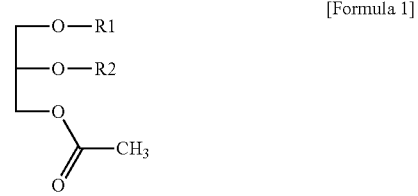

[Formula 1]

wherein R1 and R2 are independently a fatty acid residue of 14 to 22 carbon atoms.

In the present invention, the glycerol derivatives of Formula 1 are sometimes referred to as monoacetyldiacylglycerols (MDAG). Fatty acid residue refers to the acyl moiety resulting from the formation of an ester bond by reaction of a fatty acid and an alcohol. Non-limiting examples of $R_1$ and $R_2$ thus include palmitoyl, oleoyl, linoleoyl, linolenoyl, stearoyl, myristoyl, arachidonoyl, and so on. Preferable combinations of $R_1$ and $R_2$ ($R_1/R_2$) include oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl, and so on. In terms of optical activity, the monoacetyldiacylglycerol derivatives of Formula 1 can be (R)-form, (S)-form or a racemic mixture, and may include their stereoisomers. Where the $R_1$ and/or $R_2$ substituents are unsaturated fatty acid residues, the double bond(s) may have the cis configuration.

In one embodiment, the monoacetyldiacylglycerol is a compound of Formula 2:

[Formula 2]

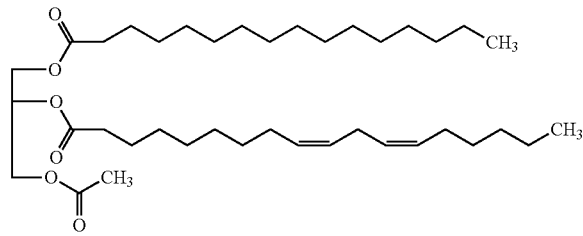 [SMILES: CCCCC/C=C\C/C=C\CCCCCCCC(=O)OC(CCOC(C)=O)COC(=O)CCCCCCCCCCCCCCC]

The compound of Formula 2 is 1-palmitoyl-2-linoleoyl-3-acetylglycerol, sometimes referred to as "PLAG" in this specification. $R_1$ and $R_2$ of the compound of Formula 2 are palmitoyl and linoleoyl, respectively. The 2-carbon on the glycerol moiety is chiral. PLAG is generally provided as the racemate, and the R- and S-enantiomers appear to have the same activity.

The monoacetyldiacylglycerol compounds can be separated and extracted from the natural deer antler or can be produced by conventional organic synthesis methods. More specifically, deer antler is extracted with hexane, followed by extracting the residue with chloroform and removing the chloroform to provide chloroform extracts. The volume of the solvents for this extraction is just enough to immerse the deer antler. In general, about 4-5 liters of hexane and/or chloroform for 1 kg of deer antler is used, but not limited thereto. The extracts obtained by this method are further fractionated and purified using a series of silica gel column chromatography and TLC methods to obtain the monoacetyldiacylglycerol compound for the present invention. An eluent for the purification step of the chromatography may be selected from among chloroform/methanol, and hexane/ethylacetate/acetic acid, but not limited thereto.

A chemical synthetic method for the preparation of monoacetyldiacylglycerol compounds is shown, for example, in WO 2013/043009 and US 20150266803, the contents of which are incorporated herein by reference. For example, PLAG can be synthesized by acylating the hydroxy groups of glycerin with acetyl, palmitoyl and linoleoyl functional groups. The final product is similar to the natural component identified and isolated from deer antlers. Both are racemates.

In the present invention, the term "treatment" or "treating" encompasses prophylaxis, reduction, amelioration or elimination of the condition to be treated, for example suppression or improvement of the symptoms of paroxysmal nocturnal hemoglobinuria (PNH).

The monoacetyldiacylglycerol compounds, especially PLAG, reduce complement activation. Without being bound to any theory, it is believed that the compounds suppress C3 by inhibiting the activity of STAT6, which may be up-regulated or activated by chemotherapy. A STAT6 inhibitor would block the STAT6 signal transduction in the cell by IL-4, which in turn would suppress expression of C3. Selective reduction of complement activity using the monoacetyldiacylglycerol compounds of Formula 1, especially PLAG, thus contributes to their effectiveness against PNH by reducing complement-mediated destruction of erythrocytes and complement-mediated damage to endothelia resulting in clot formation.

Pharmaceutical compositions comprising monoacetyldiacylglycerols may consist of only or substantially pure monoacetyldiacylglycerol derivatives of Formula 1, or may include active components (monoacetyldiacylglycerol derivatives of Formula 1) and conventional pharmaceutically acceptable carriers, excipients, or diluents. The amount of monoacetyldiacylglycerol in the pharmaceutical composition can be widely varied without specific limitation, and is specifically 0.0001 to 100 weight %, e.g., 0.001 to 50 weight %, 0.01 to 20 weight %, or 95-99 weight % with respect to the total amount of the composition. The pharmaceutical composition may be formulated into solid, liquid, gel or suspension form for oral or non-oral administration, for example, tablet, bolus, powder, granule, capsule such as hard or soft gelatin capsule, emulsion, suspension, syrup, emulsifiable concentrate, sterilized aqueous solution, non-aqueous solution, freeze-dried formulation, suppository, and so on. In formulating the composition, conventional excipients or diluents such as filler, bulking agent, binder, wetting agent, disintegrating agent, and surfactant can be used. The solid formulation for oral administration includes tablet, bolus, powder, granule, capsule and so on, and the solid formulation can be prepared by mixing one or more of the active components and at least one excipient such as starch, calcium carbonate, sucrose, lactose, gelatin, and so on. Besides the excipient, a lubricant such as magnesium stearate and talc can also be used. The liquid formulation for oral administration includes emulsion, suspension, syrup, and so on, and may include conventional diluents such as water and liquid paraffin or may include various excipients such as a wetting agent, sweetening agent, flavoring agent, and preserving agent. The formulation for non-oral administration includes sterilized aqueous solution, non-aqueous solution, freeze-dried formulation, suppository, and so on, and solvents for such solutions may include propylene glycol, polyethylene glycol, vegetable oil such as olive oil, and ester for syringe injection such as ethyl oleate. Base materials of the suppository may include witepsol, macrogol, tween 61, cacao butter, Laurin and glycerogelatine.

The monoacetyldiacylglycerol compound can be administered in a pharmaceutically effective amount. The term "pharmaceutically effective amount" is used to refer to an amount that is sufficient to achieve a desired result in a medical treatment. The "pharmaceutically effective amount" can be determined according to the subject's category, age, sex, type and severity of disease, activity of drug, sensitivity to drug, administration time, administration route, excretion rate, and so forth.

The preferable amount of the composition of the present invention can be varied according to the condition and weight of the patient, severity of disease, formulation type of drug, administration route and period of treatment. An appropriate total amount of administration per 1 day can be determined by a physician within the proper range of medical determination, and is generally about 0.05 to 200 mg/kg. Extrapolating from in vivo experiments in animals and in vitro experiments in cells, the preferable total administration amount per day is determined to be 0.1 to 100 mg/kg for an adult human. For example, the total amount of 50 mg/kg can be administered once a day or can be administered in divided doses twice, three, or four times daily.

For example, in one embodiment, the present invention provides a novel pharmaceutical composition in unit dose form, in the form of a soft gelatin capsule for oral administration containing 250-1000 mg, e.g., 500 mg, of PLAG drug substance, free of other triglycerides, together with 0.1-3 mg, e.g., 1 mg of a pharmaceutically acceptable tocopherol compound, e.g., α-tocopherol, as an antioxidant, e.g., for administration once or twice a day, e.g., at a daily dosage of 500 mg to 4,000 mg, for example, 1000 mg/day administered as a divided dose of 500 mg in the morning and 500 mg in the evening.

The present invention provides, in one aspect, a method (Method 1) for treating, (e.g. inhibiting, reducing, controlling, mitigating, or reversing) paroxysmal nocturnal hemoglobinuria (PNH), comprising administering to a patient in need thereof an effective amount (e.g. a complement-inhibiting amount) of a compound of Formula 1:

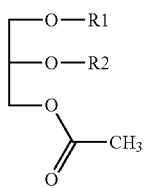

wherein $R_1$ and $R_2$ are independently a fatty acid group of 14 to 22 carbon atoms, e.g., PLAG; for example, 1.1. Method 1 wherein $R_1$ and $R_2$ are independently selected from the group consisting of palmitoyl, oleoyl, linoleoyl, linolenoyl, stearoyl, myristoyl, and arachidonoyl.

1.2. Method 1 or 1.1 wherein R1 and R2 (R1/R2) is selected from the group consisting of oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, and myristoyl/oleoyl.

1.3. Any foregoing method wherein the compound of Formula 1 is a compound of Formula 2 (PLAG):

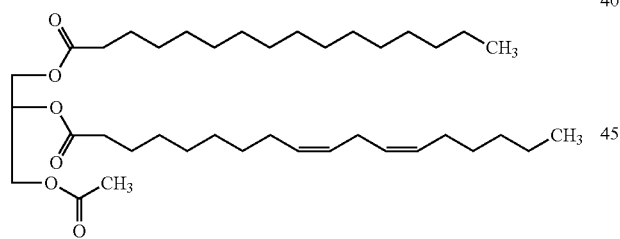

1.4. Any foregoing method wherein the compound of Formula 2 is administered in a pharmaceutical composition which is substantially free of other monoacetyldiacylglycerols, e.g, wherein at least 95%, for example, at least 99% of the total monoacetyldiacylglycerols in the formulation are of Formula 2.

1.5. Any foregoing method wherein the compound of Formula 2 is administered in a pharmaceutical composition which is substantially free of other monoacetyldiacylglycerol compounds.

1.6. Any foregoing method wherein the compound of Formula 2 is administered in a pharmaceutical composition which is substantially free of other triglyceride compounds.

1.7. Any foregoing method wherein the compound of Formula 1 is separated and extracted from natural deer antler.

1.8. Any foregoing method wherein the compound of Formula 1 is produced by chemical synthesis.

1.9. Any foregoing method wherein the compound of Formula 1 is administered in the form of a pharmaceutical composition for oral administration.

1.10. Any foregoing method wherein the compound of Formula 1 is administered in the form of a pharmaceutical composition which is a soft gelatin capsule containing the compound of Formula 1 in combination or association with a pharmaceutically acceptable diluent or carrier, for example, wherein the pharmaceutically acceptable diluent or carrier comprises an edible oil, e.g., a vegetable oil, for example, olive oil.

1.11. Any foregoing method wherein the compound of Formula 1 is administered in the form of a pharmaceutical composition comprising 0.0001 to 100.0 weight %, for example, 50-95%, or 95-99%, by weight of the composition.

1.12. Any foregoing method wherein the composition further comprises a pharmaceutically acceptable antioxidant, for example ascorbic acid (AA, E300) and tocopherols (E306), as well as synthetic antioxidants such as propyl gallate (PG, E310), tertiary butylhydroquinone (TBHQ), butylated hydroxyanisole (BHA, E320) and butylated hydroxytoluene (BHT, E321), for example α-tocopherol.

1.13. Any foregoing method wherein the compound of Formula 1 is a compound of Formula 2 administered in the form of a soft gelatin capsule containing 250 mg of the compound of Formula 2 in combination or association with approximately 50 mg of a pharmaceutically acceptable diluent or carrier, for example, an edible oil, e.g., a vegetable oil, e.g., olive oil.

1.14. Any foregoing method wherein the compound of Formula 1 is administered in the form of a functional food, for example, as an additive or admixture to a food suitable for human consumption.

1.15. Any foregoing method wherein the compound of Formula 1 is administered once a day (q.d.) or twice a day (b.i.d.).

1.16. Any foregoing method wherein the total daily dosage of the compound of Formula 1 is 250 mg to 2000 mg/day, for example, 500 mg-1500 mg/day, e.g., 500 mg/day, 1000 mg/day, or 1500 mg/day.

1.17. Any foregoing method wherein the compound of Formula 1 is administered in a dosage of 500 mg twice a day, e.g., in the morning and evening.

1.18. Any foregoing method wherein the compound of Formula 1 is administered in a dosage of 500 mg once a day, e.g., in the evening.

1.19. Any of the foregoing methods wherein the compound of Formula 1 is administered over a period of at least two weeks, e.g., at least a month.

1.20. Any foregoing method wherein the pharmaceutical composition may be formulated into solid, liquid, gel or suspension form for oral or non-oral administration.

1.21. Any foregoing method wherein the compound of Formula 1 is a compound of Formula 2 (PLAG), administered once or twice a day, at a total oral daily dosage of 500 mg to 4,000 mg.

1.22. Any foregoing method wherein the compound of Formula 1 is a compound of Formula 2 (PLAG), administered in the form of a soft gelatin capsule for oral administration containing 500 mg of PLAG drug substance and 1 mg α-tocopherol as an antioxidant, administered once or twice a day, at a total daily dosage of 500 mg to 4,000 mg.

1.23. Any foregoing method wherein the patient has a somatic mutation of a gene encoding an enzyme involved in the biosynthesis of glycosyl phosphatidylinositol (GPI).

1.24. Any foregoing method wherein the patient has a somatic mutation of a gene encoding phosphatidylinositol N-acetylglucosaminyltransferase subunit A (PIGA).

1.25. Any foregoing method wherein the patient exhibits reduced or absent levels of CD55 and CD59 presentation on erythrocytes, e.g., wherein flow cytometry for CD55 and CD59 is used to categorize erythrocytes as type I, II, or III, wherein type I cells have normal levels of CD55 and CD59; type II have reduced levels; type III have absent levels, and a PNH patient in need of treatment is one with type II or type III erythrocytes.

1.26. Any foregoing method wherein the patient exhibits reduced or absent levels of GPI on erythrocyte membranes, e.g., wherein fluorescein-labelled proaerolysin (FLAER) is used to measure GPI levels on the erythrocytes.

1.27. Any foregoing method wherein the patient exhibits red or dark discoloration of the urine due to the presence of hemoglobin and hemosiderin from the breakdown of red blood cells, anemia, tiredness, shortness of breath, palpitations, abdominal pain, difficulty swallowing and pain during swallowing, erectile dysfunction, headache, hypertension, pulmonary hypertension, and/or blood clots.

1.28. Any foregoing method wherein the patient has received or is scheduled to receive allogeneic bone marrow transplantation.

1.29. Any foregoing method wherein the patient is additionally receiving treatment selected from among one or more of the following: complement-inhibiting monoclonal antibody, e.g., eculizumab, blood transfusions, PDE5 inhibitors, and/or corticosteroids.

The present invention additionally provides a compound of Formula 1, e.g., PLAG, (pharmaceutical composition, e.g., as herein described, comprising an effective amount of a compound of Formula 1, e.g., PLAG) for use in treating, (e.g. inhibiting, reducing, controlling, mitigating, or reversing) paroxysmal nocturnal hemoglobinuria (PNH), e.g., for use in any of Methods 1, et seq.

The present invention additionally provides the use of a compound of Formula 1, e.g., PLAG, in the manufacture of a medicament for treating, (e.g. inhibiting, reducing, controlling, mitigating, or reversing) paroxysmal nocturnal hemoglobinuria (PNH), e.g., as set forth in any of Methods 1, et seq.

As used throughout, ranges are used as shorthand for describing each and every value that is within the range. Any value within the range can be selected as the terminus of the range. In addition, all references cited herein are hereby incorporated by reference in their entirety. In the event of a conflict in a definition in the present disclosure and that of a cited reference, the present disclosure controls. Unless otherwise specified, all percentages and amounts expressed herein and elsewhere in the specification should be understood to refer to percentages by weight. The amounts given are based on the active weight of the material.

MODE FOR CARRYING OUT THE INVENTION

The following examples are provided for better understanding of this invention. However, the present disclosure is not limited by the examples.

Example 1 In Vitro Inhibition of Complement Activation Pathway

PLAG's activity for regulating complement activity is achieved by suppressing production of C3. The production of C3 depends on the activity of STAT6. Thus, it is hypothesized that PLAG suppresses the activity of STAT6, and thereby suppresses the production of C3, which is up-regulated or activated by chemotherapy.

Dephosphorylation of STATE in PLAG Treated Cells:

Dephosphorylation of STAT6 is examined using anti-phosphorylated STAT6 in U937, A549, and Jurkat cell lysates treated with PLAG at a concentration from 0.01 to 10 μg/ml. Phosphorylation of STAT6 is induced by treatment with 10 ng/ml of IL-4. Dephosphorylation of STAT1 is examined in the U937 cell lysate treated with PLAG (0.01 to 10 μg/ml). Phosphorylation of STAT1 is induced by 10 ng of IFN-γ treatment. Dephosphorylation of STAT1 and STAT6 is examined at 15 min after stimulation with IFN-γ and IL-4 respectively, in the PLAG pretreated cells. Western blot analysis shows activities of STAT6 and STAT1. The transcriptional activity of STAT6 is decreased by the dephosphorylation of STAT6. In the lymphoma-derived cell line U937, T cell-derived Jurkat cells, and lung epithelial cell line A549, IL-4 treatment induced STAT6 phosphorylation is inhibited with increasing PLAG concentrations. No effect of PLAG on STAT1 phosphorylation is observed.

Activity of STAT6:

By using STAT6 inhibitor (S6I), it is confirmed that the reduction of complement 3 in HepG2 cells (human hepatocyte cell line) is regulated by STAT6. When treating HepG2 cells with PLAG, the transcriptional activity of STAT6 is gradually decreased in accordance with the amount of PLAG as confirmed by a luciferase activity study. It is also confirmed that PLAG has selective efficacy on STAT6 over STAT1. FIG. 1 presents graphs showing STAT1 and STAT6 transcriptional activity in the PLAG treated HepG2 cells. NC refers to the unstimulated control cell. For the STAT1 assay, gene transfected HepG2 (human hepatocyte cell line) is treated with 10 ng of IFN-γ and serially diluted PLAG is added (0.01 μg/ml, 0.1 μg/ml, 1 μg/ml, and 10 μg/ml as shown) to see its effect on gene expression in the stimulated cell. For the STAT6 assay, gene transfected HepG2 cells are treated with 10 ng of IL-4 and again serially diluted PLAG is added (0.01 μg/ml, 0.1 μg/ml, 1 μg/ml, and 10 μg/ml as shown) to see its effect on gene expression in the stimulated cell. The assay is carried out following a 12 hour incubation of treated cells. PLAG has no effect on STAT1 expression in this assay, but has a significant, dose-dependent effect on STAT6 expression.

In Vitro Inhibition of C3 Expression in Human HMC-1 Cells:

Published reports on the role of a complement-dependent mechanism in drug induced leukopenia and the role of neutrophils in vascular inflammation and the response to sepsis suggest that complement activation may be involved in the thrombocytopenia and leukopenia induced by chemotherapy. We have found that PLAG can down-regulate C3 to attenuate complement activation; PLAG treated human monocyte cells (HMC-1) and PLAG treated hepatocytes (HepG2) show reduced expression of C3.

A blood cell line, HMC-1 (human mast cell, American Type Culture Collection, ATCC, Rockville, Md.) is incubated and maintained at 37° C. under 5% $CO_2$ humid conditions. The medium is IMDM (Life Technologies, Karlsruhe, Germany) containing 10% Fetal Calf Serum (FCS, HyClone, Logan, Utah), 2 mM L-glutamate, 100

μg/ml penicillin, 100 μg/ml streptomycin (Life Technologies). The cultured HMC-1 cells ($1\times10^6$ cell/ml) are pretreated with 0.1 and 1 μg/mL concentrations of PLAG, followed by treatment with IL-4 (5 ng) and/or TNF-α (10 ng) to induce cellular activities.

The expressed C3 and its mRNA level changes are observed by using RT-PCR (Reverse Transcriptase Polymerase Chain Reaction). The RT-PCR is carried out as follows: the total RNA is separated by the standard protocol and cDNA is synthesized using AccuScript High Fidelity 1st Strand cDNA Synthesis Kit (Stratagene). Two-step RT-PCR reaction is conducted using Oligo-dT primer and reverse transcriptase, pair of primers and Taq polymerase (Takara, Shiga, Japan). The synthesized cDNA (1 μl) is used for a 20 μl PCR reaction with 0.5 U ExTaq DNA polymerase, 1 buffer and 1 mM dNTP mix (Takara) and the primer pair. PCR amplification is conducted under the following conditions using GeneAmp PCR system 2700 (Applied Biosystems, Foster city, CA, USA): 5 minutes at 94° C., followed by 45 seconds at 94° C., 45 seconds at 56° C. and 1 minute at 72° C. with 25-40 cycles and the final extension reaction is performed for 7 minutes at 72° C. The PCR primer used for cDNA amplification is designed with the Primer3 program, and purchased from Bioneer (Daejeon, KOREA). The product of PCR is separated using 1.5% agarose gel, dyed with ethidium bromide (EtBr), and visualized with Gel Doc 2000 UV trans-illuminator (Bio-Rad Laboratories, Hercules, Calif., USA), and the experimental data is analyzed using Quantity One software (Bio-Rad Laboratories). Western blots show that treatment of HMC-1 cell with IL-4 and TNF-α results in expression of C3, which is suppressed by PLAG on a concentration dependent basis, comparable to cells treated with IL-4 and TNF-α, followed by treatment with S6I (signal transducer and activator of transcription 6 (STAT6) inhibitor, AS1517499, Axon Medchem, Netherlands). STAT6 inhibitor blocks the STAT6 signal transduction in the cell by IL-4, which in turn suppresses expression of C3. These data suggest that PLAG may work in a manner similar to the STAT6 inhibitor.

Figure 2:
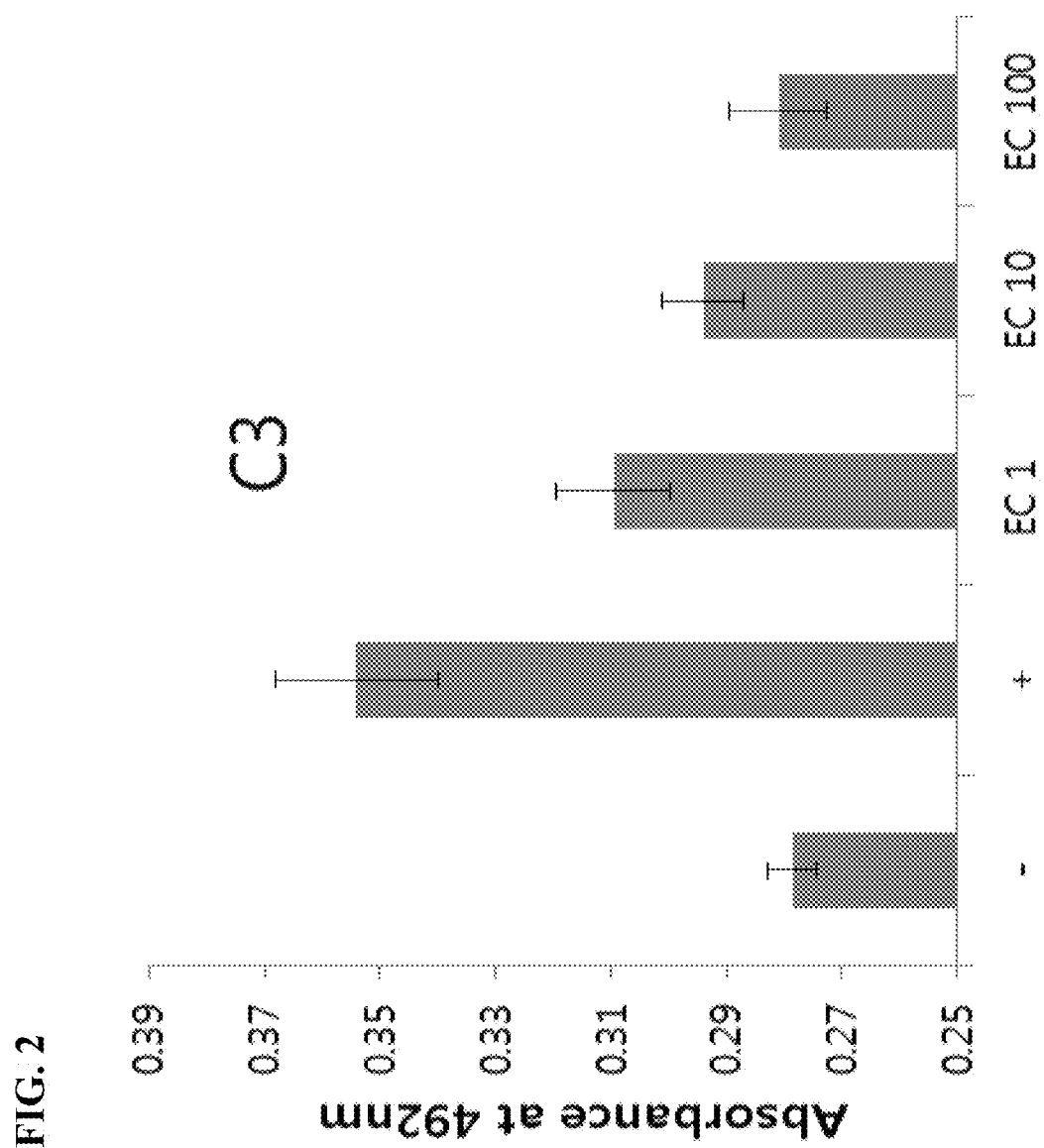
FIG. 2 depicts complement 3 inhibition by PLAG in HMC-1 cells.

C3 Inhibition by PLAG in HMC-1:

In a separate experiment, human mast cells (HMC-1, $1\times10^5$ cell/ml) are treated with PLAG of various concentrations (1, 10 and 100 μg/mL) for 2 hours. The cells are activated for 72 hours with 10% FBS (Fetal bovine serum) containing IMDM. The decrease of C3 is confirmed by ELISA analysis of the expressed protein. As shown in FIG. 2, the decrease of C3 is proportional to the concentration of PLAG (PLAG is referred to as EC in that figure; units are μg/ml).

C3 Excretion from HepG2 Cell Line:

A liver cell line, HepG2 (American Type Culture Collection, ATCC, Rockville, Md.), is incubated and maintained at 37° C., 5% $CO_2$ humid atmosphere in DMEM medium. When HepG2 cells, which are known to produce complement in culture, are treated with PLAG, the activity of complement is reduced effectively, as confirmed by RT-PCR of mRNA. In the RT-PCR, $5\times10^5$ HepG2 cells/ml are distributed into 12 well plates and induced C3 for 12 hours with 10% FCS. Then PLAG is added and further cultured for 2 hours. Cells are harvested and mRNA is isolated and RT-PCR is carried out with specific primers for C3; GAPDH is used as an internal control. The RT-PCR shows that PLAG inhibits C3 expression somewhat at 1 μg/ml and entirely at 10 μg/ml, comparable to results obtained with 10 and 100 μg/ml of S6I.

Figure 3A:
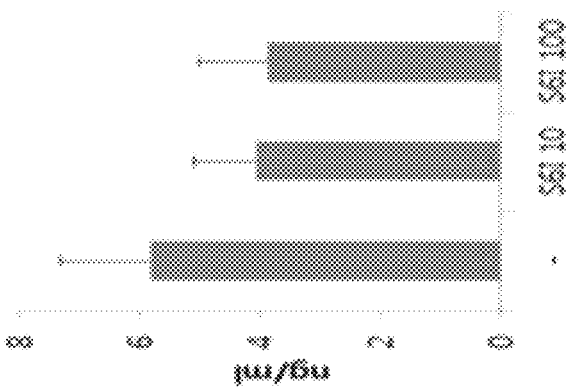
FIG. 3A confirms that PLAG does not affect the cellular propagation and death in the WST-1 assay in a HepG2 cell line.
Figure 3B:
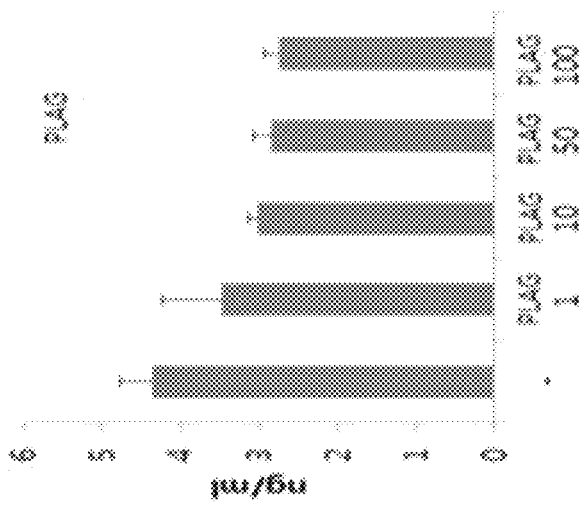
FIG. 3B shows that expression of C3 is decreased dose-dependently by the administration of PLAG.
Figure 3C:
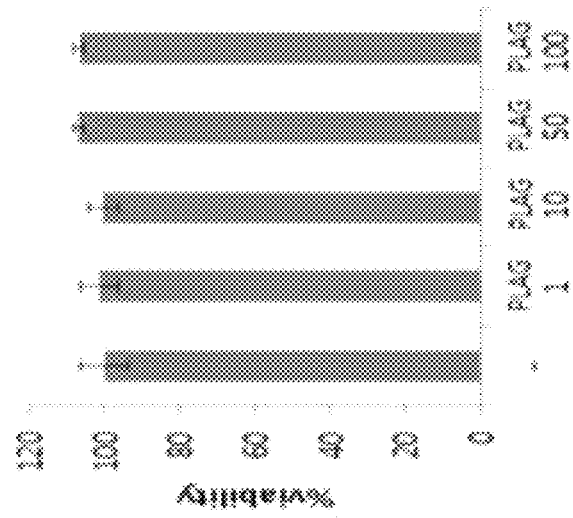
FIG. 3C shows that a similar result is obtained by the administration of S6I.

The incubated HepG2 cell lines are treated with PLAG (1~100 μg/ml), followed by IL-4 and TNF-α, reacted for 1 hour, incubated for 18 hours at 37° C. and the supernatant is isolated. Quantitation of the amount of C3 in the cellular culture medium (supernatant) from HepG2 cells is performed by ELISA using a commercially available monoclonal antibody (mAb, R&D Systems) and the manufacture's protocol; the results are presented in FIGS. 3A-3C. C3 is expressed spontaneously under in vitro culture conditions using 10% FCS added to HepG2 cells and incubated for 12 hr. The cells are treated with PLAG from 1 to 100 μg/ml (FIG. 3A, FIG. 3B) or 10 and 100 μg/ml of S6I (FIG. 3C), reacted with IL-4 and TNF-α for 1 hr and then incubated for 18 hr at 37° C. Cellular viability is confirmed using the WST-1 assay (FIG. 3A). This assay shows cell viability measured by the formation of fluorescent material, formazan, from tetrazolium salts (WST-1) by the deoxygenase in mitochondria in the cell. FIG. 3A confirms that PLAG does not affect cellular propagation and death. FIG. 3B shows that expression of C3 is decreased dose-dependently by the administration of PLAG and FIG. 3C shows that a similar result is obtained by the administration of S6I.

Example 2—In Vivo Effect of PLAG on Thrombocytopenia and Complement Activation In Vivo in Mice Colony Forming Units (CFUs) in Spleen Assay In Vivo:

In order to determine the in vivo effect of PLAG on the recovery of hematopoiesis, a CFUs assay is performed in heavily irradiated mice. A microscopic examination of the spleens of mice treated with PLAG at a dose of 50 mg/kg/d i.p. or p.o. reveals a marked increase in the number of splenic nodules and the numbers of primitive progenitor cells and megakaryocytes in all treated animals.

Figure 4:
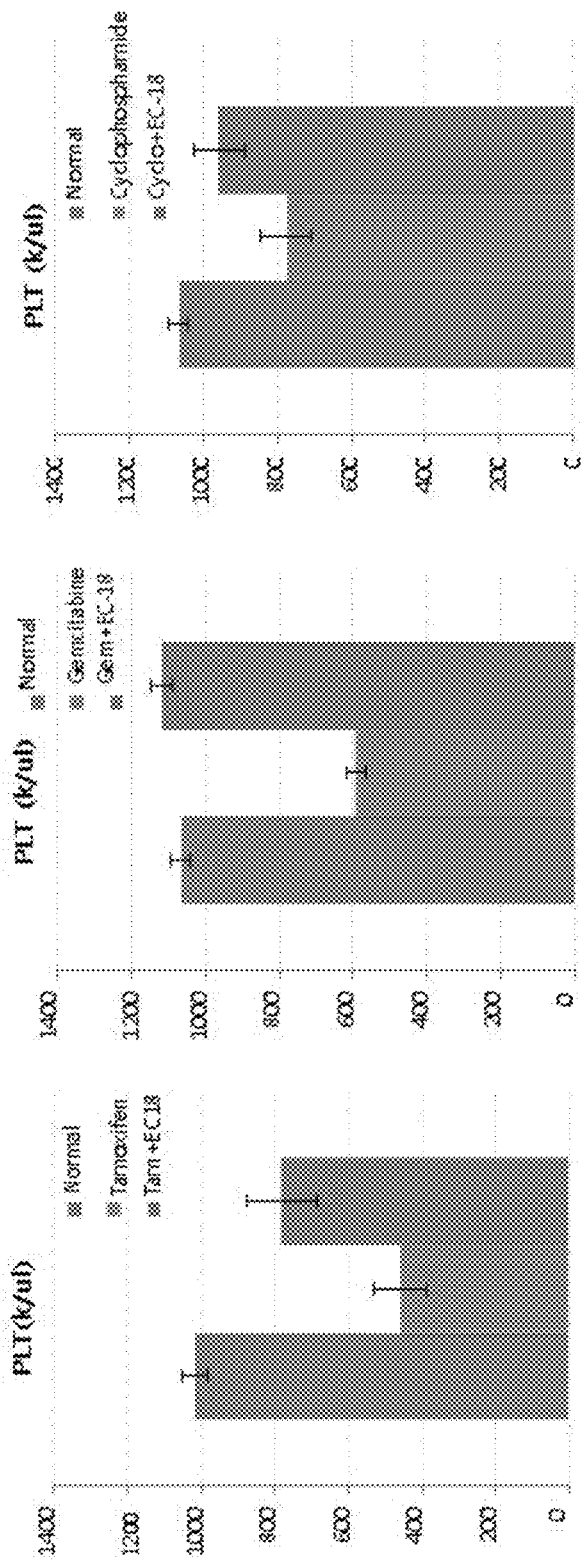
FIG. 4 depicts the platelet-protective effects of PLAG against three chemotherapeutic agents in a mouse model.

In Vivo Efficacy Study in Mice:

The effect of PLAG for treatment of chemotherapy-induced thrombocytopenia (CIT) is evaluated in an animal model. Anti-cancer agents (Gemcitabine 50 mg/kg, Cyclosphosphamide 100 mg/kg, or Tamoxifen 50 mg/kg) are dosed daily for 3 weeks; PLAG is also administered at 50 mg/kg daily for 3 weeks. Data on platelet counts is depicted in FIG. 4, showing that PLAG provides a similar protective effect for platelets against Gemcitabine 50 mg/kg, Cyclosphosphamide 100 mg/kg, or Tamoxifen 50 mg/kg.

Figure 5:
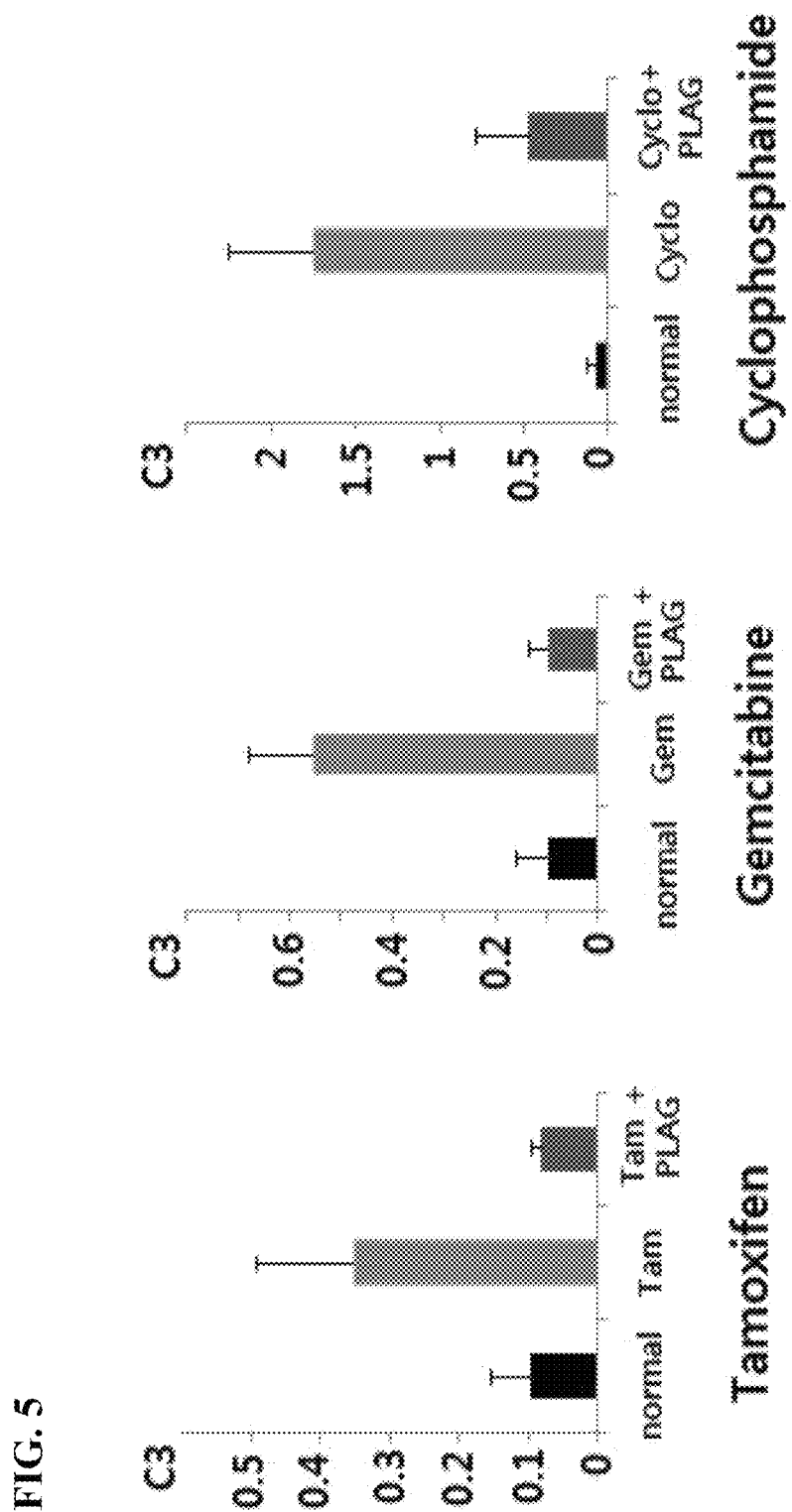
FIG. 5 depicts the complement 3 activation effects of three chemotherapeutic agents in a mouse model, and the blockage of these effects by PLAG.

It is believed that the leukopenia and thrombocytopenia of these agents and other chemotherapeutic agents may be due at least in part to a specific complement-mediated toxicity. This is seen in FIG. 5. All of these agents significantly activate complement 3, and this activity is largely blocked by PLAG.

Example 3—In Vivo Protection Against Thrombocytopenia in Mice

To evaluate the effect of PLAG on the concentration of platelets, mice are treated with compounds which would be expected to cause reductions in platelet numbers, specifically phenylhydrazine, tamoxifen or lipopolysaccharide.

Mice are injected with 100 mg/kg phenylhydrazine (PHZ), i.p., to induce anemia and reduction of platelets. 5 mg/kg PLAG is administered to the mice orally and blood samples are taken at 3 and 13 days after. In addition, for comparison, normal mice which are not treated with phenylhydrazine are prepared as a normal group, and mice treated with PHZ and olive oil instead of PLAG are prepared as a control group. The blood samples taken from the mice are treated with 0.5 ml EDTA (Minicollect tube, Greiner bio-one, Austria) and the concentration of platelets is measured using automated blood sample analyzer BC-6800 (Mindray, Shenzhen, China), by number of platelet per mL (k: 1,000). The results are shown in Table 1.

TABLE 1

|  | normal | PHZ + oil treated control group (day 3) | PHZ + PLAG treated group (day 3) |
|---|---|---|---|
| Platelet (day 3) Conc (k/ul) | 964.4 ± 57.4 | 851 ± 44.5 | 1072 ± 125.4 |
| Platelet (day 13) Conc (k/ul) | 1002.4 ± 36.8 | 1051 ± 55.4 | 1188.8 ± 115.6 |

The experiment is repeated using Tamoxifen (Tam), an anticancer agent, injected at an amount of 100 mg/kg, or lipopolysaccharide (LPS), an inflammation inducer, at an amount of 1 mg/kg to induce platelet reduction. Platelet concentration is measured 15 hours after PLAG treatment. For comparison, olive oil and PBS are used instead of PLAG as controls, respectively for the Tamoxifen and lipopolysaccharide experiment. The results are shown in Tables 2 and 3.

TABLE 2

|  | normal | Tam + oil treated Control group (after 15 hours) | Tam + PLAG (5 mg/kg) treated group (after 15 hours) |
|---|---|---|---|
| Platelet Conc. (k/ul) | 1015.7 ± 33.5 | 459 ± 171.1 | 780.7 ± 195.9 |

TABLE 3

|  | normal | LPS + PBS | LPS + PLAG(1 mg/kg) | LPS + PLAG(2 mg/kg) |
|---|---|---|---|---|
| Platelet Conc. (k/ul) | 1005.50 ± 140.7 | 423.33 ± 55.2 | 450.00 ± 101.8 | 553.33 ± 42.0 |

The normal platelet concentration is 400 to 1600 k/μl and it can vary depending on environment. Tables 1-3 shows that when thrombocytopenia is induced artificially by the administration of these compounds, the platelet concentration in the blood decreases and upon administration of PLAG to these patients, the platelet concentration is recovered.

Example 4—Clinical Study: Activity of PLAG on Complement 3

Figure 6:
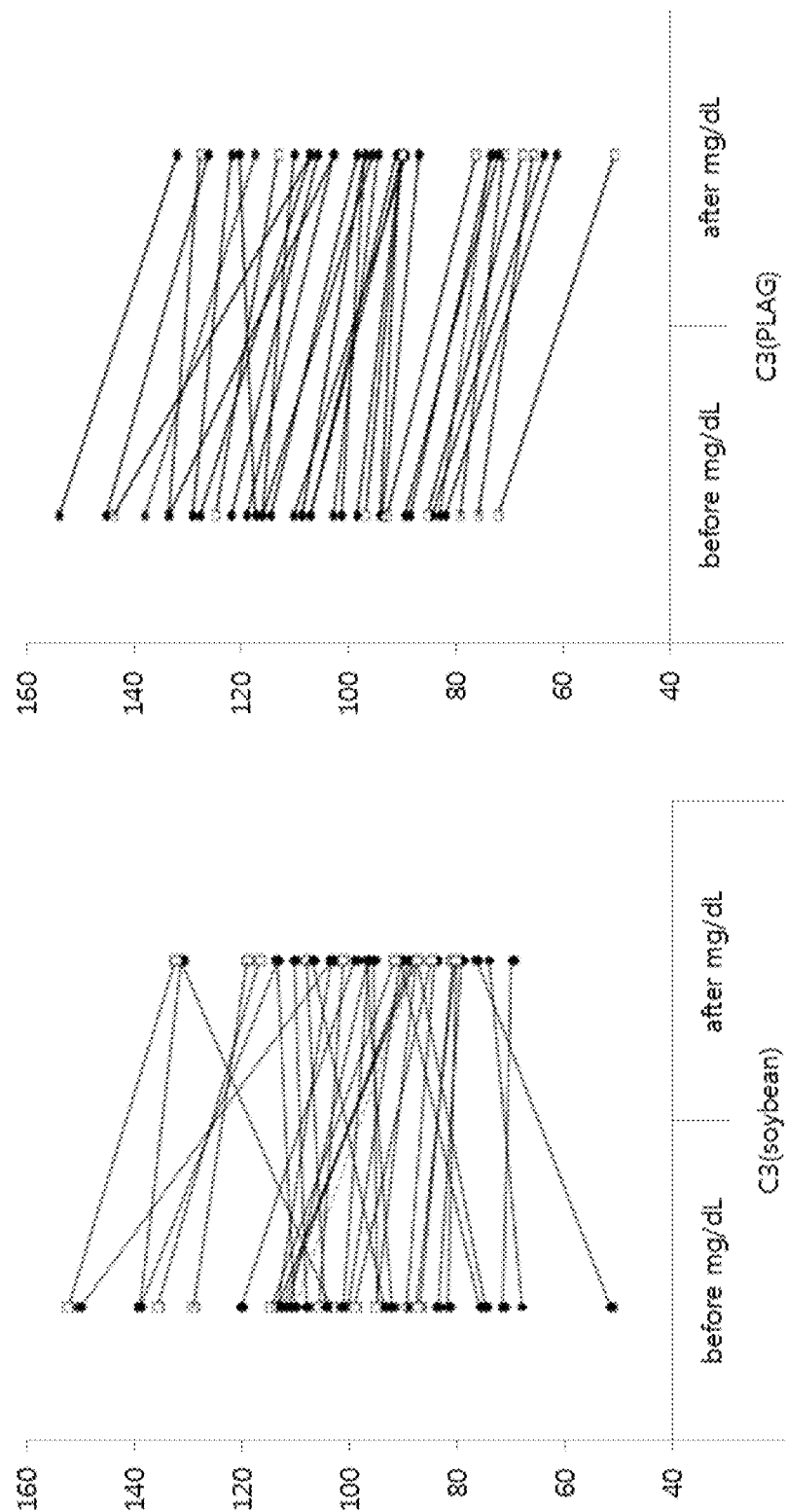
FIG. 6 depicts the results of a clinical trial on the activity of PLAG on complement 3.

A clinical study is conducted in Gwandong University MyungJi Hospital Clinical Study Center in Republic of Korea with 27 healthy patients to study the immune-modulating effect of PLAG. Volunteers are tested for 30 days in vivo as oral administration (500 mg of PLAG per day) under a legitimate clinical approval. Complement 3 is counted using a C3 assay kit. The analysis results are shown in FIG. 6, and the change in immunoactivity by the administration of PLAG in healthy subjects is shown in Table 4 (effect of PLAG supplementation on immune function of peripheral blood after 4-wk intervention). As shown in Table 4, the majority of those who consume PLAG for a month (twenty-six (26) subjects out of 27 patients) show decreased complement 3 (C3), while the control group, who are treated with soybean oil, show both increase and decrease of C3. The average concentration of C3 in blood shows a decrease of about 10 mg/dL after administration of PLAG with p value of <0.001.

TABLE 4

|  | Control (n = 22) | | | PLAG (n = 27) | | |
|---|---|---|---|---|---|---|
|  | Before | After | P value | Before | After | P-value |
| C3, mg/dl | 102.6 ± 22.5 | 97.5 ± 13.4 | 0.131 | 109.5 ± 13.0 | 99.7 ± 12.4 | <0.001 |
| C4, mg/dl | 19.6 ± 5.7 | 19.6 ± 5.5 | 0.927 | 21.6 ± 6.6 | 20.8 ± 5.6 | 0.187 |

Example 5—Unit Dosage Formulation

An exemplary soft gelatin capsule for use in the methods described herein, containing (i) PLAG and (ii) α-tocopherol, is prepared, having a composition as follows:

TABLE 5

| Composition of PLAG Softgel Capsules | | |
|---|---|---|
| Component | Function | Unit Formula |
| PLAG | Active Ingredient | 500.0 mg |
| α-tocopherol | Anti-oxidant | 1.0 mg |

TABLE 6

| Composition of Soft Capsule Shells | |
|---|---|
| Ingredients | Function |
| Gelatin | Capsule shell |
| Concentrated glycerin | Plasticizer |
| Methyl para-oxybenzoate | Preservative |
| Propyl para-oxybenzoate | Preservative |
| Ethyl vanillin | Flavor |
| Titanium dioxide | Colorant |
| Tar color, MFDS notified Blue No. 1 | Colorant |

TABLE 6-continued

Composition of Soft Capsule Shells

| Ingredients | Function |
| --- | --- |
| Tar color, MFDS notified Red No. 40 | Colorant |
| Tar color, MFDS notified Yellow No. 203 | Colorant |
| Purified water | Vehicle |

The invention claimed is:

1. A method for treating paroxysmal nocturnal hemoglobinuria (PNH), comprising administering to a patient in need thereof an effective amount of a compound of Formula 1:

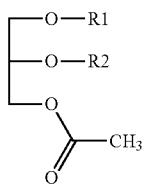

wherein R1 and R2 are independently a fatty acid residue of 14 to 22 carbon atoms.

2. The method of claim 1 wherein R1 and R2 are independently selected from the group consisting of palmitoyl, oleoyl, linoleoyl, linolenoyl, stearoyl, myristoyl, and arachidonoyl.

3. The method of claim 1 wherein R1 and R2 (R1/R2) is selected from the group consisting of oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, and myristoyl/oleoyl.

4. The method of claim 1 wherein the compound of Formula 1 is a compound of Formula 2:

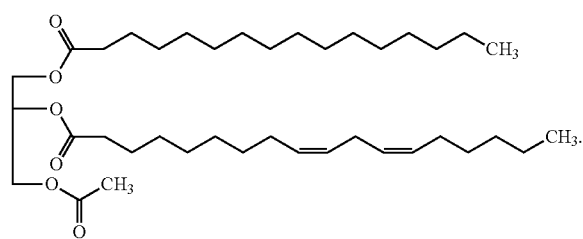 [SMILES: CCCCC/C=C\C/C=C\CCCCCCCC(=O)OC(CCOC(C)=O)COC(=O)CCCCCCCCCCCCCCC]

5. The method of claim 4 wherein the compound of Formula 2 is administered in a pharmaceutical composition which is substantially free of other monoacetyldiacylglycerol compounds.

6. The method of claim 5 wherein the compound of Formula 2 is administered in a pharmaceutical composition which is substantially free of triglyceride compounds.

7. The method of claim 1 wherein the effective amount of the compound of Formula 1 is a complement-inhibiting amount.

8. The method of claim 1 wherein the compound of Formula 1 is administered in the form of a pharmaceutical composition which is a soft gelatin capsule containing the compound of Formula 1.

9. The method of claim 1 wherein the compound of Formula 1 is a compound of Formula 2 (PLAG), administered once or twice a day, at a total oral daily dosage of 500 mg to 4,000 mg.

10. The method of claim 1 wherein the compound of Formula 1 is a compound of Formula 2 (PLAG), administered in the form of a soft gelatin capsule for oral administration containing 500 mg of PLAG drug substance and 1 mg α-tocopherol as an antioxidant, administered once or twice a day, at a total daily dosage of 500 mg to 4,000 mg.

11. The method of claim 1 wherein the patient has a somatic mutation of a gene encoding phosphatidylinositol N-acetylglucosaminyltransferase subunit A (PIGA).

12. The method of claim 1 wherein the patient exhibits reduced or absent levels of CD55 and CD59 presentation on erythrocytes.

13. The method of claim 1 wherein the patient exhibits reduced or absent levels of GPI on erythrocyte membranes.

14. The method of claim 1 wherein the patient exhibits red or dark discoloration of the urine due to the presence of hemoglobin and hemosiderin from the breakdown of red blood cells, anemia, tiredness, shortness of breath, palpitations, abdominal pain, difficulty swallowing and pain during swallowing, erectile dysfunction, headache, hypertension, pulmonary hypertension, and/or blood clots.

15. The method of claim 1 wherein the patient has received or is scheduled to receive allogeneic bone marrow transplantation.

16. The method of claim 1 wherein the patient is additionally receiving treatment selected from one or more of the following: complement-inhibiting monoclonal antibody, blood transfusions, PDE5 inhibitors, and/or corticosteroids.

17. The method of claim 1 wherein the patient is a human.

18. The method of claim 1 wherein the patient is identified as suffering from paroxysmal nocturnal hemoglobinuria and the compound of claim 1 is administered to the identified patient.

19. The method of claim 4 wherein the patient is identified as suffering from paroxysmal nocturnal hemoglobinuria and the compound of claim 1 is administered to the identified patient.

* * * * *